(12) United States Patent
Lewis et al.

(10) Patent No.: US 6,350,369 B1
(45) Date of Patent: Feb. 26, 2002

(54) METHOD AND SYSTEM FOR DETERMINING ANALYTE ACTIVITY

(75) Inventors: Nathan S. Lewis, La Canada; Thomas P. Vaid, Pasadena, both of CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/291,932

(22) Filed: Apr. 13, 1999

Related U.S. Application Data

(60) Provisional application No. 60/081,781, filed on Apr. 14, 1998.

(51) Int. Cl.[7] .............................................. G02N 27/26
(52) U.S. Cl. .................... 205/777.5; 205/775; 205/787; 204/403; 204/412; 422/82.02
(58) Field of Search ................................ 204/403, 400, 204/412, 406; 205/775, 777.5, 787, 792, 793.5; 422/82.01, 82.02

(56) References Cited

U.S. PATENT DOCUMENTS

| | | | | |
|---|---|---|---|---|
| 4,644,154 A | * | 2/1987 | Brogardh et al. | 250/277.23 |
| 4,927,502 A | * | 5/1990 | Reading et al. | 205/777.5 |
| 5,246,846 A | * | 9/1993 | Pittner et al. | 435/174 |
| 5,250,264 A | * | 10/1993 | Walt et al. | 422/82.07 |
| 5,466,348 A | | 11/1995 | Holm-Kennedy | 204/153.1 |
| 5,571,401 A | | 11/1996 | Lewis et al. | 205/787 |
| 5,653,939 A | | 8/1997 | Hollis et al. | 422/50 |
| 5,698,089 A | | 12/1997 | Lewis et al. | 205/787 |
| 5,846,744 A | * | 12/1998 | Athey et al. | 435/7.9 |

FOREIGN PATENT DOCUMENTS

| | | | |
|---|---|---|---|
| WO | 9424561 | * | 10/1994 |

OTHER PUBLICATIONS

Williams et al. ("Resolving combustible gas mixtures using gas sensitive resistors with arrays of electrodes", J. Chem. Soc., Faraday Trans., 1996, 92(22), 4497–4504).*

Wehrens et al. (Calibration of an array of voltammetric microelectrodes, Analytica Chimica Acta, 334 (1996) 93–101).*

Luinge et al., "Trace–level identity confirmation from infra-red spectra by library searching and artificial neural networks", Analytica Chimica Acta 345 (1997) 173–184.

Dickinson et al., "Generating sensor diversity through combinatorial polymer synthesis", Analytical Chemistry, vol. 69, No. 17, Sep. 1, 1997.

Doleman et al., "Quantitative study of the resolving power of arrays of carbon black–polymer composites in various vapor–sensing tasks" Analytical Chemistry, vol. 70., No. 19, Oct. 1, 1998.

Lipman, "E–noses nose out traditional odor–detection equipment" EDN, pp. 59–62, Dec. 17, 1998.

* cited by examiner

Primary Examiner—T. Tung
Assistant Examiner—Alex Noguerola
(74) Attorney, Agent, or Firm—Gray Cary Ware & Freidenrich LLP; Lisa A. Haile

(57) ABSTRACT

Chemical sensors for detecting the activity of a molecule or analyte of interest is provided. The chemical sensors comprise and array or plurality of chemically-sensitive resistors that are capable of interacting with the molecule of interest, wherein the interaction provides a resistance fingerprint. The fingerprint can be associated with a library of similar molecules of interest to determine the molecule's activity.

26 Claims, 9 Drawing Sheets

| alcohol | experimental pI50 | run# (bubbler #) | polymer name sensor #: | poly(4-vinylpyridine) 1 |
|---|---|---|---|---|
| 1-butanol | −0.05 | 1 (8) | | 0.23 (0.08) |
| 1-heptanol | 0.68 | 2 (6) | | 0.05 (0.1) |
| 1-hexanol | 0.54 | 3 (6) | | 0.09 (0.08) |
| 1-pentanol | 0.27 | 3 (7) | | 0.17 (0.1) |
| 1-propanol | −0.48 | 3 (3) | | 0.55 (0.14) |
| 2, 4-dimethyl-3-pentar | −1.38 | 2 (1) | | 0.05 (0.14) |
| 2-butanol | −0.35 | 2 (8) | | 0.2 (0.13) |
| 2-heptanol | 0.25 | 1 (2) | | 0.13 (0.08) |
| 2-hexanol | 0.15 | 2 (2) | | 0.16 (0.15) |
| 2-methyl-1-butanol | −0.15 | 2 (7) | | 0.04 (0.11) |
| 2-methyl-1-propanol | −0.39 | 1 (6) | | 0.12 (0.07) |
| 2-methyl-3-pentanol | −0.89 | 1 (1) | | 0.13 (0.09) |
| 2-pentanol | −0.07 | 3 (8) | | 0.06 (0.06) |
| 2-propanol | −0.47 | 1 (7) | | 0.24 (0.08) |
| 3-hexanol | −0.47 | 3 (1) | | 0.07 (0.08) |
| 3-methyl-butanol | −0.19 | 3 (5) | | 0.08 (0.08) |
| 3-pentanol | −0.37 | 2 (4) | | 0.11 (0.09) |
| ethanol | −1.1 | 2 (3) | | 1.52 (0.15) |
| menthanol | −3.09 | 1 (3) | | 3.71 (0.23) |
| neopentanol (solid) | −0.67 | 3 (2) | | 0.03 (0.1) |
| | | | | |
| | | | | |
| benzyl alcohol | 0.32 | 1 (4) | | 0.06 (0.07) |
| tert-amyl alcohol | −2.56 | 1 (5) | | 0.1 (0.1) |
| 1, 3-propanediol | −1.87 | 3 (4) | | −0.02 (0.1) |
| 1, 4-butanediol | −1.41 | 2 (5) | | −0.01 (0.09) |

FIG. 5A

| poly(vinyl chloride) | poly(ethylene oxide) | poly(styrene/allyl alcohol) | poly(4-vinylphenol) | poly(vinyl acetate) | ethyl cellulose |
|---|---|---|---|---|---|
| 2 | 3 | 4 | 5 | 6 | 7 |
| 0.01 (0.15) | 1.83 (0.22) | 0.56 (0.08) | 0.41 (0.17) | 0.11 (0.08) | 4.04 (0.2) |
| 0.04 (0.16) | 1.9 (0.1) | 0.23 (0.02) | 0.08 (0.11) | −0.07 (0.05) | 4.28 (0.21) |
| 0.03 (0.16) | 1.76 (0.04) | 0.45 (0.05) | 0.11 (0.09) | −0.08 (0.05) | 5.32 (0.18) |
| −0.03 (0.13) | 1.63 (0.02) | 0.58 (0.05) | 0.16 (0.1) | 0.02 (0.04) | 4.97 (0.14) |
| −0.03 (0.19) | 1.18 (0.01) | 0.57 (0.04) | 0.7 (0.09) | 0.2 (0.03) | 3.17 (0.14) |
| −0.02 (0.13) | 2 (0.06) | 0.17 (0.02) | 0.1 (0.11) | 0 (0.03) | 4.94 (0.25) |
| −0.06 (0.12) | 1.35 (0.04) | 0.65 (0.1) | 0.29 (0.23) | 0.14 (0.05) | 3.89 (0.29) |
| −0.04 (0.09) | 2.89 (0.54) | 0.28 (0.04) | 0.11 (0.13) | −0.09 (0.05) | 4.76 (0.18) |
| 0.01 (0.15) | 1.69 (0.09) | 0.37 (0.03) | 0.17 (0.11) | −0.05 (0.03) | 5.1 (0.31) |
| 0.02 (0.12) | 1.74 (0.05) | 0.34 (0.04) | 0.16 (0.14) | −0.01 (0.04) | 4.76 (0.27) |
| 0.01 (0.12) | 1.84 (0.15) | 0.48 (0.08) | 0.28 (0.14) | 0.1 (0.03) | 3.98 (0.2) |
| 0.06 (0.11) | 2.34 (0.33) | 0.29 (0.05) | 0.19 (0.11) | −0.03 (0.04) | 5.24 (0.26) |
| −0.03 (0.13) | 1.41 (0.02) | 0.57 (0.07) | 0.14 (0.09) | 0 (0.07) | 4.9 (0.19) |
| 0.13 (0.14) | 1.58 (0.23) | 0.57 (0.06) | 0.62 (0.17) | 0.14 (0.06) | 3.31 (0.31) |
| 0.01 (0.13) | 1.57 (0.03) | 0.4 (0.04) | 0.07 (0.08) | −0.06 (0.05) | 5.56 (0.23) |
| 0.03 (0.08) | 1.49 (0.02) | 0.39 (0.03) | 0.07 (0.07) | 0.01 (0.04) | 4.82 (0.13) |
| 0.08 (0.15) | 1.52 (0.04) | 0.55 (0.06) | 0.16 (0.13) | −0.01 (0.05) | 4.83 (0.41) |
| 0.19 (0.14) | 1.08 (0.02) | 0.59 (0.05) | 2.19 (0.17) | 0.31 (0.03) | 2.19 (0.14) |
| 0.57 (0.12) | 1.33 (0.1) | 0.55 (0.03) | 2.51 (0.21) | 0.4 (0.07) | 1.82 (0.22) |
| 0 (0.18) | 1.37 (0.04) | 0.14 (0.03) | −0.01 (0.05) | 0.02 (0.03) | 3.28 (0.2) |
| | | | | | |
| | | | | | |
| 0.04 (0.13) | 3.05 (0.91) | 0.22 (0.03) | 0.1 (0.07) | −0.03 (0.05) | 2.07 (1.01) |
| −0.07 (0.14) | 1.77 (0.24) | 0.39 (0.07) | 0.26 (0.14) | 0.06 (0.05) | 3.91 (0.29) |
| 0.04 (0.12) | 0.17 (0.02) | 0.06 (0.02) | −0.01 (0.05) | 0.01 (0.03) | 0.4 (0.19) |
| −0.01 (0.15) | 0.19 (0.2) | 0.06 (0.06) | 0.04 (0.06) | −0.02 (0.04) | 0.81 (0.68) |

FIG. 5B

| poly(N-vinylpyrrolidone) | poly(ethylene/acrylic acid) | poly(ethylene/vinyl acetate) | poly(methyl methacrylate) | poly(methylvinylether/ maleic anhydride) | 1,2polybutadiene |
|---|---|---|---|---|---|
| 8 | 9 | 10 | 11 | 12 | 13 |
| 0.31 (0.7) | 1.65 (0.14) | 0.74 (0.1) | 0 (0.02) | −0.01 (0.01) | 0.23 (0.1) |
| 0.52 (0.84) | 1.66 (0.09) | 0.69 (0.04) | 0.01 (0.03) | 0 (0.01) | 0.3 (0.02) |
| −0.07 (0.6) | 1.84 (0.05) | 0.73 (0.02) | 0.01 (0.03) | −0.01 (0.02) | 0.28 (0.01) |
| 0.67 (0.58) | 1.7 (0.03) | 0.67 (0.01) | 0.01 (0.02) | 0 (0.02) | 0.21 (0.01) |
| 1.08 (0.82) | 1.07 (0.02) | 0.4 (0.02) | 0.01 (0.03) | −0.02 (0.02) | −0.03 (0.01) |
| 0.11 (0.61) | 2.49 (0.05) | 2.42 (0.09) | 0.02 (0.02) | 0.03 (0.02) | 1.19 (0.04) |
| 0.23 (0.68) | 1.62 (0.03) | 0.76 (0.04) | 0 (0.03) | −0.02 (0.01) | 0.26 (0.01) |
| 0.23 (0.99) | 1.91 (0.06) | 0.99 (0.04) | 0 (0.03) | 0.01 (0.03) | 0.45 (0.02) |
| 0.77 (0.42) | 1.97 (0.05) | 0.92 (0.03) | −0.01 (0.02) | 0.1 (0.02) | 0.45 (0.01) |
| 0.09 (0.73) | 1.82 (0.04) | 0.91 (0.03) | −0.01 (0.02) | −0.01 (0.01) | 0.41 (0.01) |
| 0.47 (0.59) | 1.65 (0.1) | 0.78 (0.08) | 0 (0.02) | −0.04 (0.02) | 0.28 (0.07) |
| 0.76 (0.61) | 2.17 (0.02) | 1.59 (0.04) | 0 (0.03) | 0.08 (0.02) | 0.75 (0.02) |
| 0.68 (0.55) | 1.77 (0.02) | 0.82 (0.02) | −0.01 (0.02) | 0 (0.01) | 0.34 (0.01) |
| 0.4 (0.88) | 1.45 (0.07) | 0.63 (0.04) | 0 (0.02) | −0.04 (0.03) | 0.16 (0.05) |
| 0.02 (1.03) | 1.81 (0.04) | 1.07 (0.01) | 0.01 (0.02) | 0.01 (0.02) | 0.51 (0.01) |
| 0.08 (0.83) | 1.77 (0.02) | 0.75 (0.02) | −0.01 (0.04) | −0.04 (0.02) | 0.36 (0.01) |
| −0.13 (0.81) | 1.79 (0.03) | 1.03 (0.04) | −0.01 (0.01) | −0.01 (0.02) | 0.43 (0.01) |
| 4.03 (0.74) | 0.78 (0.3) | 0.2 (0.04) | 0.14 (0.03) | −0.03 (0.02) | −0.13 (0.03) |
| 7.76 (0.78) | 0.69 (0.03) | 0.15 (0.04) | 0.57 (0.03) | 0.52 (0.05) | −0.01 (0.01) |
| −0.13 (0.79) | 1.54 (0.05) | 0.94 (0.03) | 0 (0.03) | 0 (0.02) | 0.42 (0.01) |
| | | | | | |
| | | | | | |
| −0.1 (0.59) | 0.58 (0.34) | 0.33 (0.17) | −0.01 (0.02) | −0.04 (0.02) | 0.11 (0.08) |
| 0.35 (0.62) | 2.05 (0.12) | 1.04 (0.08) | 0 (0.02) | −0.03 (0.02) | 0.47 (0.06) |
| −0.39 (0.8) | 0.06 (0.01) | 0.02 (0.02) | −0.01 (0.04) | −0.03 (0.02) | 0.02 (0.01) |
| −0.09 (0.79) | 0.14 (0.15) | 0.05 (0.05) | −0.01 (0.02) | −0.03 (0.02) | 0.03 (0.02) |

FIG. 5C

| poly(styrene/ acrylonitrile) | poly(methyloctadccy-lisoxane) | poly(vinyl butyral) | poly(ethylene glycol) | poly(2,4,6-tribromostyrene) | polystyrene |
|---|---|---|---|---|---|
| 15 | 16 | 17 | 18 | 19 | 20 |
| 0 (0) | 0.42 (0.02) | 1.14 (0.27) | 2.37 (0.25) | 0.12 (0.06) | -0.46 (0.73) |
| 0 (0) | 0.41 (0.03) | 0.45 (0.22) | 1.23 (0.14) | 0.01 (0.02) | -0.01 (0.82) |
| 0 (0) | 0.49 (0.02) | 0.89 (0.14) | 1.79 (0.08) | 0.04 (0.03) | 0.23 (0.94) |
| 0.01 (0) | 0.46 (0.02) | 1.04 (0.18) | 1.95 (0.06) | 0.07 (0.06) | -0.21 (0.8) |
| 0.02 (0) | 0.28 (0.02) | 1.15 (0.2) | 2.12 (0.11) | 0.25 (0.04) | 0.47 (0.59) |
| 0 (0.01) | 0.72 (0.02) | 0.54 (0.21) | 1.85 (0.04) | 0.01 (0.02) | -0.29 (0.69) |
| 0 (0) | 0.4 (0.02) | 1.03 (0.23) | 1.95 (0.09) | 0.13 (0.02) | 0.17 (0.32) |
| 0 (0) | 0.49 (0.03) | 0.62 (0.19) | 2.13 (0.49) | 0.03 (0.01) | -0.03 (0.32) |
| 0.01 (0) | 0.51 (0.01) | 0.77 (0.21) | 1.73 (0.11) | 0.03 (0.02) | 0.08 (0.76) |
| 0 (0.01) | 0.45 (0.02) | 0.77 (0.24) | 2.08 (0.11) | 0.03 (0.03) | 0.15 (0.84) |
| 0 (0) | 0.41 (0.02) | 1.01 (0.21) | 2.41 (0.19) | 0.09 (0.05) | 0.2 (0.5) |
| 0.01 (0) | 0.59 (0.02) | 0.7 (0.2) | 2.34 (0.25) | 0.03 (0.03) | -0.09 (0.84) |
| 0 (0) | 0.45 (0.02) | 1.03 (0.28) | 1.85 (0.07) | 0.07 (0.05) | -0.12 (0.79) |
| 0 (0) | 0.36 (0.03) | 1.15 (0.17) | 2.34 (0.29) | 0.14 (0.04) | -0.04 (0.47) |
| 0 (0) | 0.53 (0.02) | 0.87 (0.2) | 1.63 (0.1) | 0.06 (0.08) | -0.12 (0.74) |
| 0 (0) | 0.42 (0.02) | 0.9 (0.12) | 1.85 (0.06) | 0.03 (0.03) | -0.09 (0.73) |
| 0 (0) | 0.5 (0.03) | 0.96 (0.31) | 1.85 (0.1) | 0.07 (0.04) | 0.14 (0.71) |
| 0.17 (0.01) | 0.23 (0.02) | 1.44 (0.25) | 2.14 (0.1) | 0.42 (0.04) | -0.11 (0.63) |
| 0.62 (0.03) | 0.21 (0.02) | 1.58 (0.25) | 2.78 (0.2) | 0.27 (0.03) | 0.11 (0.7) |
| 0 (0) | .034 (0.02) | 0.39 (0.2) | 1.75 (0.07) | 0.01 (0.03) | -0.21 (0.56) |
|  |  |  |  |  |  |
|  |  |  |  |  |  |
| 0 (0) | 0.17 (0.11) | 0.34 (0.26) | 1.36 (0.48) | 0.01 (0.04) | -0.5 (0.76) |
| 0 (0) | 0.46 (0.01) | 0.74 (0.16) | 2.26 (0.23) | 0.08 (0.03) | 0.09 (0.48) |
| 0 (0) | 0.01 (0.02) | 0.09 (0.18) | 0.09 (0.09) | 0 (0.13) | 0.04 (0.78) |
| 0 (0.01) | 0.04 (0.04) | 0 (0.14) | 0.13 (0.13) | 0.01 (0.03) | -0.32 (0.87) |

FIG. 5D

METHOD AND SYSTEM FOR DETERMINING ANALYTE ACTIVITY

CROSS REFERENCE TO RELATED APPLICATIONS

This application claims the benefit of the U.S. Provisional Application No. 60/081,781, filed on Apr. 14, 1998, which is incorporated herein by reference.

FIELD OF THE INVENTION

The present invention relates to a sensor apparatus useful in detecting trace analytes in a sample, and more specifically determining the analyte's biological or physical activity.

BACKGROUND OF THE INVENTION

There exists a need for determining a variety of molecular properties that are important in determining a biological, a chemical, or a physical property or activity of a molecule and cataloging these properties so that they can be used to identify candidate lead molecules for a biological, chemical, pharmaceutical, or industrial application of interest.

Currently methods are used to screen potential drug compounds or biologics from a collection of molecules of interest (e.g., a library). Such methods use assay techniques that detect a specific activity based on a molecule's binding affinity, enzymatic activity or other properties. Alternatively, lead compounds are generated by computational methods, wherein the molecules that possess certain desirable properties are defined by shape, dipole moments, surface area, solubility, vapor pressure, hydrophobicity, hydrophilicity, antigenicity and other physical properties. These chemical-physical properties are then defined and used to computationally narrow lead compounds to a manageable subset which are then analyzed further by additional screening techniques designed to measure a specific activity in vitro or in vivo by using additional high throughput screening techniques.

Generation of lead compounds is important because not only does it allow for exploration of a wider range of potential pharmaceutical agents, but it also offers opportunities for construction of follow-up libraries that focus on the molecular characteristics represented by these lead molecules. This in turn is performed to provide yet more leads with the desired pharmaceutical activity eventually with the hope of finding a candidate suitable for clinical use.

SUMMARY OF THE INVENTION

The present invention provides a method for identifying a specific activity, structure or function of a molecule of interest based on a sensing device. The sensing device includes an array of sensors responsive to a molecule's physical, chemical, or biological characteristics. The differentially responsive sensors can be optical sensors, resonance mechanic frequency sensors, and/or electrical sensors to name a few. Other sensors and arrays are known to those of skill in the art. For example, in one embodiment the sensing device includes a chemical sensor comprising first and second conductive elements (e.g. electrical leads) electrically coupled to a chemically sensitive resistor which provides a selective electrical path between the conductive elements. The resistor comprises a plurality of alternating non-conductive regions (comprising a non-conductive material) and conductive regions (comprising a conductive material) in series. The electrical path between the first and second conductive elements is transverse to (i.e., passes through) a plurality of alternating non-conductive and conductive regions. In use, the resistor provides a change in resistance between the conductive elements when contacted with an analyte or molecule which interacts with the non-conductive region. The non-conductive region can be made of any material designed to interact or bind to a class, genus, or specie of analyte.

The disclosure provides a method and device for identifying a specific activity, structure or function of an analyte or molecule of interest. The method uses a sensing device to produce a characteristic experimental pattern generated by a plurality of differentially responsive sensors. The pattern has information on the desired molecular properties for a molecule or analyte of interest. A response pattern is produced for each member of the library. These patterns are then stored and associated with the library. The library contains patterns for molecules having a desired or known property or activity.

In one embodiment, a method is provided for screening samples for a specific activity or structure by measuring outputs of a plurality of chemically-sensitive resistors, each resistor comprising a conductive material and a non-conductive material; using results of said measuring to obtain a signal profile, relating to a change in resistance in the plurality of resistors; and comparing the signal profile to a previously-obtained signal profile indicating a standard sample having a specific activity, wherein the signal profile is indicative of a specific activity or a specific structure.

The disclosure additionally provides a screening system that includes a sensor array comprising a plurality of differentially responsive sensors, each sensor capable of providing a signal corresponding to the sensors interaction with a molecule of interest. A measuring device detects the signal from each sensor and arranges them into a signal profile representing a molecule's characteristics (e.g., activity, structure, or function). A computer then compares the signal profile to determine the molecule's activity. Preferably, the computer has a resident algorithm for comparing the signal profile(s).

For example, in one embodiment, a sample screening system is provided, the system including a sensor array comprising at least first and second chemically-sensitive resistors, each chemically-sensitive resistor comprising a mixture of non-conductive organic polymer and conductive material compositionally different than said non-conductive organic polymer, each resistor providing an electrical path through said mixture of non-conductive organic polymer and said conductive material, a first electrical resistance, when contacted with a first chemical analyte at a first concentration and a second different electrical resistance when contacted with a second analyte, wherein the difference between the first electrical resistance and the second electrical resistance of the first chemically-sensitive resistor being different from the difference between the first electrical resistance and the second electrical resistance of the second chemically-sensitive resistor; an electrical measuring device electrically connected to the sensor array; and a computer wherein the electrical measuring device detects the first and second electrical resistance in each of the chemically-sensitive resistors and the computer assembles the resistance into a sensor array signal profile, wherein the computer is operative to compare the signal profile to a signal profile obtained from a standard sample having a specific activity, wherein the signal profile is indicative of a specific activity or a specific structure.

BRIEF DESCRIPTION OF THE DRAWING

These and other objects of the present invention will now be described in detail with reference to the accompanying drawing, in which:

FIG. 5 shows a table where the first three columns give the name of the alcohol, its experimental $pI_{50}$ value and run in which it was analyzed (and the bubbler in which it was placed). The remainder of the table lists the responses (expressed as percent change in electrical resistance relative to base line resistance) of the 19 different polymer/carbon black sensors upon exposure to the alcohols at 5% of their respective saturated vapor pressures. The standard deviation of the responses over ten trials are given in parenthesis. Sensor 14 was not functioning. The last four alcohols were not used in building the model.

DESCRIPTION OF THE PREFERRED EMBODIMENTS

Figure 1A:
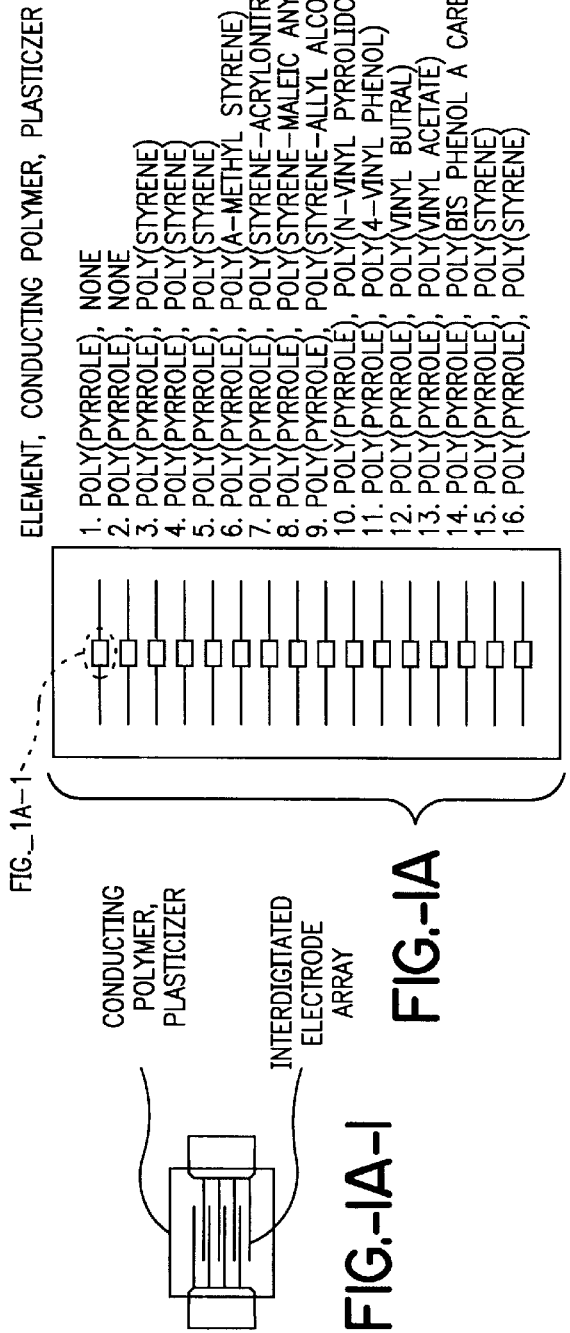
FIG. 1A shows an overview of sensor design; 1B, shows an overview of sensor operation; and 1C, shows an overview of system operation.
Figure 1B:
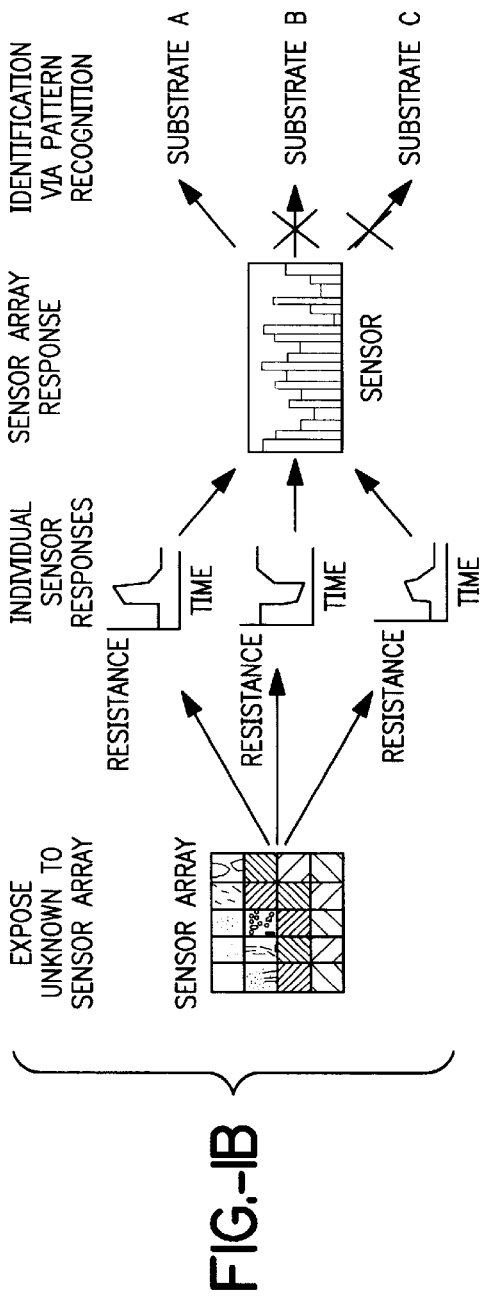
Figure 1C:
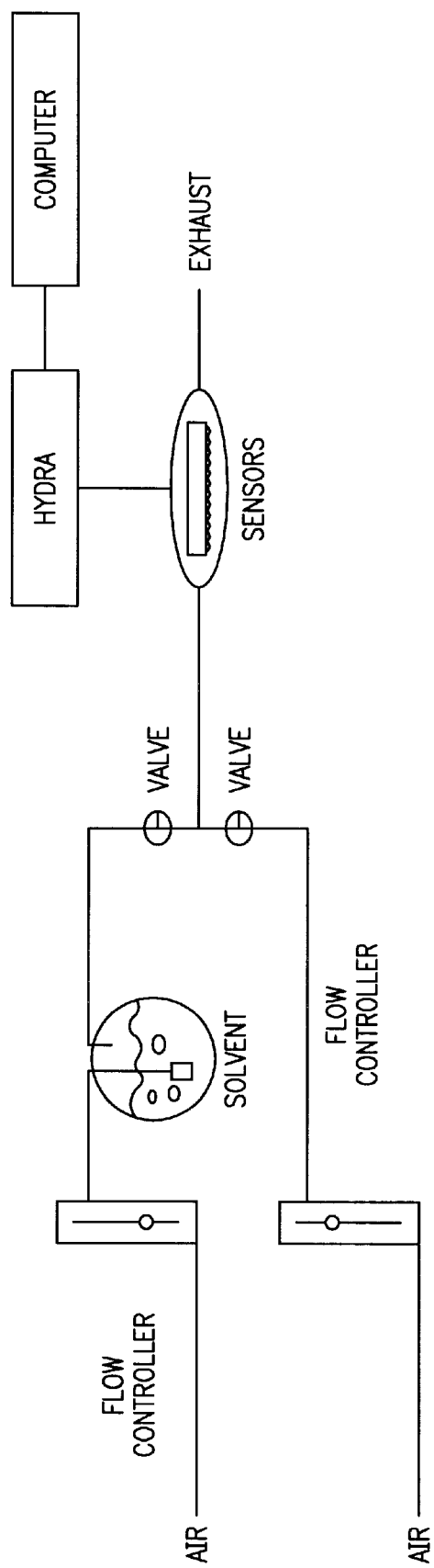

The approach described herein uses experimental data (e.g. a signal profile, such as a resistance fingerprint) that is generated by an array of differentially responsive sensors. Such sensors include, for example, chemically-sensitive resistor of a sensing array, such as that found in an "electronic nose" as described in U.S. Pat. No. 5,571,401 (the disclosure of which is incorporated herein), when it is exposed to a molecule of interest. The change in the electrical resistance of a chemically-sensitive resistor in such a sensing array can be related to the sorption of a molecule of interest to the non-conductive regions of the chemically-sensitive resistor. The signals produced by a plurality of chemically-sensitive resistors having individual sorption criteria thus provide information on a number of chemically important properties, such as the hydrophobicity, molecular size, polarity, and hydrogen-bonding interactions of a molecule of interest, thus, for example, creating a resistance profile or fingerprint of the molecule of interest based upon its chemical properties.

Another type of sensor, includes, for example, hydrogels containing a crystalline colloidal array (CCA) as disclosed in U.S. Pat. No. 5,854,078 (the disclosure of which is incorporated herein by reference). Such hydrogels undergo a volume change in response to a specific chemical species. As the hydrogels are modulated in size the lattice spacing of the CCA embedded therein changes as well. The light diffraction, therefore, indicates the presence or absence of the stimuli that causes the volume of the hydrogel to change.

Yet another type of sensor includes those disclosed in U.S. Pat. No. 5,512,490 to Walt et al. (the disclosure of which is incorporated herein by reference). The optic sensor of this system is comprised of a supporting member and an array formed of heterogeneous, semi-selective thin films which function as sensing receptor units and are able to detect a variety of different analytes and ligands using spectral recognition patterns. Each formulation of sensing receptor unit comprising the array of the optical sensor reacts with a plurality of different chemical compounds and compositions; and for each individual chemical compound, provides a spectral response pattern over time (by changes in energy intensity, or by changes in wavelength or both of these parameters) which is indicative of the event and consequence of the reaction with a single compound. The array also generates spectral responses and patterns from mixtures of different compounds based upon the optical responses from each of the individual compounds forming this mixture.

By "molecule of interest" or "analyte" is meant any number of various molecules. For example a molecule or analyte of interest may be a nucleic acid (e.g., DNA or RNA), a polypeptide (e.g., an antibody, protein, enzyme), a biochemical (e.g., a lipid, hormone, fatty acids, carbohydrate), pharmaceuticals, a chemical such as organics including, for example, alkanes, alkenes, alkynes, dienes, alicyclic hydrocarbons, arenes, alcohols, ethers, ketones, aldehydes, cyclic hydrocarbons, carbonyls, carbanions, polynuclear aromatics and derivatives of such organics, e.g., halide derivatives.

By "differentially responsive sensors" is meant any number of sensors that respond to the presence or interaction of a collection of molecules with the sensor by providing some measurable change. Each individual sensor does not uniquely probe the property of interest, thus any individual signal alone is not sufficient to determine the desired chemical or biological property of an analyte. Instead the response pattern of a plurality of sensors is used to obtain the desired activity through comparison with a standard response pattern produced by an analyte with a known activity. Such measurable changes include changes in optical wavelengths, transparency of a sensor, resonance of a sensor, resistance, diffraction of light and/or sound, and other changes easily identified to those skilled in the art. Such sensors include, but are not limited to, crystalline colloidal array (CCA) sensors and variants, such as hydrogels containing CCA, metal oxide sensors, dye-impregnated polymers coated onto beads or optical fibers, bulk conducting organic polymers, and capacitance sensors.

In a traditional assay method, a desired chemical or biological activity is determined by the response of one designed sensor or interest. This single response is known to probe the chemical and/or biological activity of interest, and the magnitude of the sensor response is then readily and directly related to the activity of concern. For instance, enzymatic inhibition by a certain ligand could be determined from an assay that probed directly the amount of substrate consumed by the enzyme under various conditions or indirectly by the amount of product metabolized under known and calibrated conditions. Different ligands would produce different amounts of substrate consumption or metabolite products, and the amounts of such would directly indicate the desired biological property, the ligand inhibition of the enzymatic activity. Another example would be determination of the presence of a particular nucleic acid sequence in a sample through investigating the response of array of sensors, each of which had complements to different but known or knowable sequences of nucleic acids. The sensor that displayed the highest response change (for instance, florescence appearance or disappearance, electrochemical activity or disappearance of electrochemical activity, etc.) would then be uniquely associated with the presence of the sequence of interest in the sample, through knowledge of the complementary sequence that was present on that particular sensing element and association of the knowledge of the complementary sequence with the sequence that must then be present in the analyte of interest.

The present invention utilizes a different approach. A plurality of differentially responsive sensors, each of which provides measurable signals in response to a variety of analytes, chemicals, and biochemicals of concern, is used. The desired chemical or biological activity is not revealed by the response of an individual sensor or individual sensor response signal, but is instead obtained by pattern analysis of the responses produced by a plurality of differentially responsive sensors in the sensor array device. The sensors may or may not themselves be selective and predetermined to uniquely probe the chemical or biological property of interest, but the various differing response patterns produced by the analytes of interest upon exposure to the plurality of sensors is correlated with the desired chemical and/or biological activity after comparison of the response pattern to the pattern produced by an analyte with a known chemical and/or biological activity.

By allowing interactions between a molecule of interest and a differentially responsive sensor, the signals can be directly or indirectly related to the properties of the molecule of interest. For example, by using a chemically-sensitive resistor in an array of an "electronic nose" it is possible to directly and indirectly relate the signals of the electronic nose to the properties of the molecules of interest. For example, if the significant interactions between a molecule and the binding site of an enzyme are related either directly or indirectly in the collection of binding constants of that molecule to a non-conductive element of the electronic nose, then it is possible to relate the electronic nose signal to the enzyme's binding properties.

Once a signature of a set of molecules has been obtained, the signature profile could be used, with an appropriate training set to predict the activity of any member of the library in a chemical interaction of interest.

As described in the Example below, which is not meant to limit the present claims, the inventor has demonstrated that an electronic nose is capable of identifying alcohols having chemical characteristics that are capable of inhibiting cytochrome P-450 activity. Such chemical characteristics are related to various chemical-physical parameters of the alcohol including its three-dimensional structure, side groups, charge, and other parameters known to those of skill in the art.

The methods and apparatus of the present invention are applicable to a wide range of molecules of interest and types of sensors and arrays. For example, and not by way of limitation, one embodiment provides a method which can be used to identify polypeptides having a biological function. Such functions include a polypeptide's role as a receptor, receptor antagonist or agonist, enzymatic activity (e.g., lipases, esterases, proteases, glycosidases, glycosyl transferases, phosphatases, kinases, mono- and dioxygenases, haloperoxidases, lignin peroxidases, diarylpropane peroxidases eposide hydrolases, nitrile hydrotasees, nitrilases, transaminases, amidases and acylases), DNA-binding ability (e.g., histones), antibody activity (e.g., the ability to bind an epitope), such antibodies include monoclonal, polyclonal and humanized antibodies to name a few. The activity can be determined based on the polypeptides primary, secondary, and/or tertiary structure as well as its charge, hydrophobicity, hydrophilicity and other polypeptide properties known to those of skill in the art as compared to a library of similar polypeptide molecules. The differentially responsive sensors (e.g., a chemically-sensitive resistor) of an array for detection of such properties are designed as described herein or in any number of ways known to those of skill in the art. The differentially responsive sensors do not need to be specially designed to bind a specific polypeptide. For example, where the sensor is of a resistor-type, the elements do not need to be specially designed to bind such polypeptides so long as they are capable of detecting properties by interactions of the polypeptide or molecule of interest with the chemically-sensitive resistor.

In another embodiment, the present invention provides a method of detecting the activity of a biological molecule or pharmaceutical compound. The method provides contacting a plurality of differentially responsive sensors with a compound or molecule of interest and then comparing the "fingerprint" (e.g., a resistance fingerprint) or "profile" with the fingerprint of other related molecules having a desired activity or function. Molecules having similar fingerprints are indicative of molecules having similar activities. Such activities can range from the detection of disease molecules (e.g., viral antigens, bacterial antigens, such as LPS, endotoxin, etc.), carcinogenic molecules, antibiotic molecules, antiviral molecules, viral compounds and any number of molecules now known or discovered, so long as they are capable of interacting with a plurality of sensors thus eliciting a change in for example, optics, resonance, and/or current across the sensor (e.g., increase or decrease in the resistance).

Learning based and/or pattern-recognition based algorithms are used to identify leads from the library based on the data contained in the experimental response patterns, without the need necessarily for additional assays or for additional computations on the remaining members of the library. Additionally, one advantage of the invention is that it provides an experimentally based measure of the molecular properties involved in the desired binding event. Once a pattern has been recorded for a library, it remains associated with that library indefinitely and can be used for other purposes subsequently. For example, after screening a library for leads in activity towards a given binding site, with a few new examples on another binding site, the patterns can then be interrogated again to produce leads for this new target event without the need to recollect the response patterns nor to reassay the entire library for activity towards that particular new process.

The differentially responsive sensors in the array need not be carefully tailored towards the molecule of interest. Instead, it is sufficient that they collectively probe a broad range of molecular properties, for example, hydrophobicity, polarity, molecular size or shape, chirality, and other chemical-physical characteristics known in the art. Each individual sensor need not selectively probe these properties, nor is it essential that the experimentalist evaluate in advance which properties are being probed by the array. For example, an array may have any number of responsive sensors from one to greater than $10^6$. In a preferred embodiment, wherein the sensors are resistors the array would have a significant (>10) number of chemically-sensitive detectors or resistors, each of which would be at least partially responsive to certain properties that affect molecular binding and recognition events.

The signal transduction mechanism through which the analyte or molecule produces an array response or resistance fingerprint is potentially quite broad. Many methods are known to those skilled in the art of constructing artificial nose devices. These include arrays of surface acoustic wave devices, quartz crystal micro-balances, dye-coated fiber optics, conducting organic polymers, electrochemical gas sensors, fiber optic micromirrors, composites of insulating organic polymers and conductors, tin oxide sensors, hydrogel based CCA, nucleic acid or protein based polymers (see for example Ramsey, Graham, Nature Biotech, 16:40–44, (1998)), and others readily identifiable to those skilled in the art. Different types of signal transduction mechanisms could also be used in one array to expand the information contained in the response pattern produced by the analyte or molecule of interest, for example optical, electrical, and/or resonance.

When the differentially responsive sensor is a resistor, the resistor comprises a plurality of alternating non-conductive and conductive regions transverse to an electrical path between conductive leads. Generally, the resistors are fabricated by blending a conductive material with a non-conductive material such that the electrically conductive path between the leads coupled to the resistor is interrupted by gaps of non-conductive material. For example, in a colloidal suspension or dispersion of particulate conductive material in a matrix of non-conductive material, the matrix regions separating the particles provide the gaps. The non-conductive gaps range in path length from about 10 to 1,000 angstroms, usually on the order of 100 angstroms providing individual resistance of about 10 to 1,000 m$\Omega$, usually on the order of 100 m$\Omega$, across each gap. The path length and resistance of a given gap is not constant but rather is believed to change as the nonconductive organic polymer of the region absorbs, adsorbs or imbibes an analyte. Accordingly the dynamic aggregate resistance provided by these gaps in a given resistor is a function of analyte permeation of the non-conductive regions. However, it will be recognized that materials which change conformationally, or effect a proton distribution or availability, in response to the binding of an analyte are also encompassed by the present disclosure. For example, a non-conductive material which results in a proton change upon binding of an analyte can cause an exponential change in the resistance of the chemically-sensitive resistor. In some embodiments, the conductive material may also contribute to the dynamic aggregate resistance as a function of analyte permeation (e.g., when the conductive material is a conductive material such as a polypryole).

A wide variety of conductive materials and non-conductive materials can be used. Table 1 provides exemplary conductive materials for use in resistor fabrication; mixtures, such as of those listed, may also be used. Table 2 provides exemplary non-conductive materials; blends and copolymers, such as the materials listed here, may also be used. Combinations, concentrations, blend stoichiometries, percolation, threshold, etc. are readily determined empirically by fabricating and screening prototype resistors (chemiresistors) as described below.

TABLE 1

| Major Class | Examples |
| --- | --- |
| Organic Conductors | conducting polymers (poly(anilines), poly(thiophenes), poly(pyrroles), poly(aceylenes, etc.)), carbnaceious material (carbon blacks, graphite, coke, C60 etc.), charge transfer complexes (tetramethylparaphnylenediamine-chloranile, alkaili metal tetracyanoquinodimethane complexes tetrathiofulvalene halide complexes, etc.), etc. |
| Inorganic Conductors | metals and metal alloys (Ag, Au, Cu, Pt, AuCu alloy, etc.), highly doped semiconductors (Si, GaAs, InP, MoS2, TiO2, etc.), conductive metal oxides (In2O3, SnO2, Na2Pt3O4, etc.), superconductors (Yba2Cu3O7, Ti2Ba2Ca2Cu3O10, etc.), etc. |

TABLE 1-continued

| Major Class | Examples |
| --- | --- |
| Mixed inorganic/organic Conductor | Tetracyanoplatinate complexes, Iridium halocarbonyl complexes, stacehed macrocyclic complexes. Etc. |

TABLE 2

| Major Class | Examples |
| --- | --- |
| Main-chain carbon polymers | poly(dienes), poly(alkenes), poly(acrylics), poly(methacrylics), poly(vinyl ethers), poly(vinyl thioethers), poly(vinyl alcohols), poly(vinyl ketones), poly(vinyl halides), poly(vinyl nitrites), poly(vinyl esters), poly(styrenes), poly(aryines), etc. |
| Main-chain acyclic heteroatom polymers | poly(oxides), poly(caronates), poly(esters), poly(anhydrides), poly(urethanes), poly(sulfonate), poly(siloxanes), poly(sulfides), poly(thioesters), poly(sulfones), poly(sulfonamindes), poly(amides), poly(ureas), poly(phosphazens), poly(silanes), poly(silazanes), etc. |
| Main-chain heterocyclic polymers | Poly(furantetracarboxylic acid diimides), poly(benzoxazoles), poly(oxadiazoles), poly(benzothiazinophenothiazines), poly(benzothiazoles), poly(pyrazinoquinoxalines), poly(pyromenitimides), poly(quinoxalines), poly(benzimidazoles), poly(oxidoles), poly(oxoisinodolines), poly(diaxoisoindoines), poly(triazines), poly(pyridzaines), poly(pioeraziness), poly(pyridinees), poly(pioeridiens), poly(triazoles), poly(pyrazoles), poly(pyrrolidines), poly(carboranes), poly(oxabicyclononanes), poly(diabenzofurans), poly(phthalides), poly(acetals), poly(anhydrides), carbohydrates, etc. |

The chemiresistors can be fabricated by many techniques such as, but not limited to, solution casting, suspension casting, and mechanical mixing. In general, solution case routes are advantageous because they provide homogenous structures and ease of processing. With solution case routes, resistor elements may be easily fabricated by spin, spray or dip coating. Since all elements of the resistor must be soluble, however, solution case routes are somewhat limited in their applicability. Suspension casting still provides the possibility of spin spray or dip coating but more heterogenous structures than with solution casting are expected. With mechanical mixing, there are fewer solubility restrictions since it involves only the physical mixing of the resistor components but device fabrication is more difficult since spin, spray and dip coating are no longer possible. A more detailed discussion of each of these follows.

For systems where both the conducting and non-conducting media or their reaction precursors are soluble in a common solvent, the chemiresistors can be fabricated by solution casting. The oxidation of pyrrole by phosphomolybdic acid presented herein represents such a system. In this reaction, the phosphomolybdic acid and pyrrole are dissolved in tetrahydrofuran (THF) and polymerization occurs upon solvent evaporation. This allows for THF soluble non-conductive polymers to be dissolved into this reaction mixture thereby allowing the blend to be formed in a single step upon solvent evaporation. The choice of non-conductive material in this route is, of course, limited to those that are soluble in the reaction media. For the poly (pyrrole) case described above, preliminary reactions were performed in THF, but this reaction should be generalizable to other non-aqueous solvent such as acetonitrile or ether. A variety of permutations on this scheme are possible for other conducting material. Some of these are listed below. Certain conducting materials, such as substituted poly (cyclooctatetraenes), are soluble in their undoped, non-conducting state in solvents such as THF or acetonitrile. Consequently, the blends between the undoped material and plasticizing material can be formed from solution casting. After which, the doping procedure (exposure to $I_2$ vapor, for instance) can be performed on the blend to render the substituted poly(cyclooctatetraene) conductive. Again, the choice of non-conductive materials is limited to those that are soluble in the solvents that the undoped conducting material is soluble in and to those stable to the doping reaction. Certain conducting materials can also be synthesized via a soluble precursor material. In these cases, blends between the precursor material and the non-conducting material can first be formed followed by chemical reaction to convert the precursor material into the desired conducting material. For instance poly(p-phenylene vinylene) can be synthesized through a soluble sulfonium precursor. Blends between this sulfonium precursor and the non-conductive material can be formed by solution casting. After which, the blend can be subjected to thermal treatment under vacuum to convert the sulfonium precursor to the desired poly(p-phenylene vinylene).

In suspension casting, one or more of the components of the resistor is suspended and the others dissolved in a common solvent. Suspension casting is a rather general technique applicable to a wide range of species, such as carbon blacks or colloidal metals, which can be suspended in solvents by vigorous mixing or sonication. In one application of suspension casting, the non-conductive material is dissolved in an appropriate solvent (such as THF, acetonitrile, water, etc.). Colloidal silver is then suspended in this solution and the resulting mixture is used to dip coat electrodes.

Mechanical mixing is suitable for all of the conductive/non-conductive combinations possible. In this technique, the materials are physically mixed in a ball-mill or other mixing device. For instance, carbon black: non-conductive material composites are readily made by ball-milling. When the non-conductive material can be melted or significantly softened without decomposition, mechanical mixing at elevated temperature can improve the mixing process. Alternatively, composite fabrication can sometimes be improved by several sequential heat and mix steps. Once fabricated, the individual elements can be optimized for a particular application by varying their chemical make up and morphologies. The chemical nature of the resistors determines to which analytes they will respond and their ability to distinguish different analytes. The relative ratio of conductive to insulating components determines the magnitude of the response since the resistance of the elements becomes more sensitive to sorbed molecules as the percolation threshold is approached. The film morphology is also important in determining response characteristics. For instance, thin films respond more quickly to analytes than do thick ones. Hence, with an empirical catalogue of information on chemically diverse sensors made with varying ratios of insulating to conducting components and by differing fabrication routes, sensors can be chosen that are appropriate for the analytes expected in a particular application, their concentrations, and the desired response times. Further optimization can then be performed in an iterative fashion as feedback on the performance of an array under particular conditions becomes available.

The resistor may itself form a substrate for attaching the lead or the resistor. For example, the structural rigidity of the resistors may be enhanced through a variety of techniques:chemical or radiation cross-linking of polymer components (dicumyl peroxide radical cross-linking, UV-radiation cross-linking of poly(olefins), sulfur cross-linking of rubbers, e-beam cross-linking of Nylon, etc.), the incorporation of polymers or other materials into the resistors to enhance physical properties (for instance, the incorporation of a high molecular weight, high transition metal (Tm) polymers), the incorporation of the resistor elements into supporting matrices such as clays or polymer networks (forming the resistor blends within poly-(methylmethacrylate) networks or within the lamellae of montmorillonite, for instance), etc. In another embodiment, the resistor is deposited as a surface layer on a solid matrix which provides means for supporting the leads. Typically, the matrix is a chemically inert, non-conductive substrate such as a glass or ceramic.

Sensor arrays particularly well-suited to scaled up production are fabricated using integrated circuit (IC) design technologies. For example, the chemiresistors can easily be integrated onto the front end of a simple amplifier interfaced to an A/D converter to efficiently feed the data stream directly into a neural network software or hardware analysis section. Micro-fabrication techniques can integrate the chemiresistors directly onto a micro-chip which contains the circuitry for analog signal conditioning/processing and then data analysis. Ink-jet technology can be used for the production of millions of incrementally-different sensor elements in a single manufacturing step. Controlled compositional gradients in the chemiresistor elements of a sensor array can be induced in a method analogous the way that a color ink-jet printer deposits and mixes multiple colors. However, in this case, rather than multiple colors, a plurality of different polymers in solution which can be deposited are used. A sensor array of a million distinct elements only requires a 1 cm×1 cm sized chip employing lithography at the 10$\mu$m feature level, which is within the capacity of conventional commercial processing and deposition methods. This technology permits the production of sensitive, small-sized, stand-alone chemical sensors.

Preferred sensor arrays have a predetermined inter-sensor variation in the structure or composition of the non-conductive polymer regions. The variation may be quantitative and/or qualitative. For example, the concentration of the non-conductive material in the blend can be varied across sensors. Alternatively, a variety of different materials may be used in different sensors. In one embodiment, an electronic nose for detecting an analyte in a sample is fabricated by electrically coupling the sensor leads of an array of compositionally different sensors to an electrical measuring device. The device measures changes in resistivity at each sensor of the array, preferably simultaneously and preferably over time. Frequently, the device includes signal processing means and is used in conjunction with a computer and data structure for comparing a given response profile to a structure-response profile database for qualitative and quantitative analysis. Typically such a nose comprises at least ten, usually at least 100, and often at least 1000 different sensors though with mass deposition fabrication techniques described herein or otherwise known in the art, arrays of on the order of at least $10^6$ sensors are readily produced.

In operation, each resistor provides a first electrical resistance between its conductive leads when the resistor is contacted with a first sample comprising a chemical analyte at a first concentration, and a second electrical resistance between its conductive leads when the resistor is contacted with a second sample comprising the same chemical analyte at a second different concentration. The samples may be liquid or gaseous in nature. The first and second samples may reflect samples from two different environments, a change in the concentration of an analyte in a sample sampled at two time points, a sample and a negative control, etc. The sensor array necessarily comprises sensors which respond differently to a change in an analyte concentration, i.e. the difference between the first and second electrical resistance of one sensor is different from the difference between the first and second electrical resistance of another sensor.

In a preferred embodiment, the temporal response of each sensor (resistance as a function of time) is recorded. The temporal response of each sensor may be normalized to a maximum percent increase and percent decrease in resistance which produces a response pattern associated with the exposure of the analyte. By iterative profiling of known analytes, a structure-function database correlating analytes and response profiles is generated. Unknown analyte may then be characterized or identified using response pattern comparison and recognition algorithms. Accordingly, analyte detection systems comprising sensor arrays, an electrical measuring device for detecting resistance across each chemiresistor, a computer, a data structure of sensor array response profiles, and a comparison algorithm are provided. In another embodiment, the electrical measuring device is an integrated circuit comprising neural network-based hardware and a analog-digital converter (ADC) multiplexed to each sensor, or a plurality of ADCs, each connected to different sensor(s).

A wide variety of analytes and samples may be analyzed by the disclosed sensors, arrays and noses so long as the subject analyte is capable of generating a differential response across a plurality of sensors of the array. Analyte applications include broad ranges of chemical classes such as organics such as alkanes, alkenes, alkynes, dienes, alicyclic hydrocarbons, arenes, alcohols, ethers, ketones, aldehydes, carbonyls, carbanions, polynuclear aromatics and derivatives of such organics, e.g. halide derivatives, etc., biomolecules such as sugars, isoprenes and isoprenoids, fatty acids and derivatives, etc. Accordingly, commercial applications of the sensors, arrays and noses include environmental toxicology and remediation, biomedicine, materials quality control, food and agricultural products monitoring, etc.

The general method for using the disclosed sensors, arrays and electronic noses, for detecting the characteristics or presence of an analyte in a sample involves sensing a change in a differentially responsive sensor to the presence of an analyte in a sample. For example, where the sensor is a resistor-type sensor, measurement in resistance changes where the chemical sensor comprises first and second conductive leads electrically coupled to and separated by a chemically-sensitive resistor as described above by measuring a first resistance between the conductive leads when the resistor is contacted with a first sample comprising an analyte at a first concentration and a second different resistance when the resistor is contacted with a second sample comprising the analyte at a second different concentration.

In one embodiment, a rapid method for individually addressing the members of the library and individually collecting their response patterns is desirable. In this embodiment, gases derived from a fluid are used wherein the analytes are vapors that are to be detected by their response on the sensor array. A substrate contains the library (e.g., analyte matrix) of interest whose response patterns are to be collected. The substrate may be cooled in order to reduce the vapors emanating from the molecules before analysis. The sensors (e.g. "chemically-sensitive resistors") are also placed within this analysis chamber. Either a carrier gas or a vacuum is present in order to insure that the chamber is not contaminated with residual molecules of a prior analysis, inlet and outlet ports may be used to manipulate and control the gas flow. The sensors themselves may also have a temperature control, as may the walls of the chamber. Cooling the walls of the chamber will prevent desorption of the impurities during an analysis and heating can be used to clean the chamber of such impurities at a subsequent time. Temperature control of the sensors is beneficial to control the sensitivity, response time, and noise characteristics of the detectors in the sensor array.

In this embodiment, the library is cooled so that the vapor pressure of each individual molecular constituent is maintained at a background level until that particular species is to be analyzed. When a response pattern is to be recorded for a molecule of interest, the region that contains the molecule of interest in the library is heated to volatilize it. This thereby produces vapors that can be transported to the detectors of the sensor array. This local heating could be performed by a laser spot, by an addressable resistive grid of wires that contacts the substrate or a portion of the substrate, or by other methods of heating that are known to those skilled in the art of generating temperature excursions in materials. After the pattern is recorded for the spot of interest, the temperature is returned to its set point and another spot is interrogated. An alternative uses multiple sets of detectors in parallel, with accompanying stimuli in parallel, to increase the throughput of analysis of an entire array if so desired.

Once a series of patterns has been collected, some initial information is desirable in order to identify leads for a particular activity or function. For example, experimental data might be available showing that members 1, 2, and 3 have increasing activity towards the activity or function of interest. Such activity or function may be derived from known molecules whose activity has been well-characterized or may be subsequently or contemporaneously measured by additional assay techniques. Analysis of the patterns produced by the electronic nose array using neural network or statistical method -based programs would then identify which molecules, or which molecular properties being probed by the detectors, showed a correlation with the specific or desired activity or function. Once this correlation is established, analysis of the remaining patterns would be used to identify molecules with similar correlation, and thereby to identify the leads in the library for further interrogation and analysis both experimentally and theoretically, as appropriate.

The analysis of a resistance signal pattern (e.g. a resistance profile) of the embodiment may be implemented in hardware or software, or a combination of both (e.g., programmable logic arrays or digital signal processors). Unless otherwise specified, the algorithms included as part of the invention are not inherently related to any particular computer or other apparatus.

In particular, various general purpose machines may be used with programs written in accordance with the teachings herein, or it may be more convenient to construct more specialized apparatus to perform the operations. However, preferably, the embodiment is implemented in one or more computer programs executing on programmable systems each comprising at least one processor, at least one data storage system (including volatile and non-volatile memory and/or storage elements), at least one input device, and at least one output device. The program code is executed on the processors to perform the functions described herein.

Each such program may be implemented in any desired computer language (including machine, assembly, high level procedural, or object oriented programming languages) to communicate with a computer system. In any case, the language may be a compiled or interpreted language.

Each such computer program is preferably stored on a storage media or device (e.g., ROM, CD-ROM, or magnetic or optical media) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

The following Example, is provided to illustrate, but not limit, the scope of the present invention. For example, those skilled in the art will recognize that the methods and systems of the present invention are applicable to a wide variety of differentially responsive sensors, including optical, sound (resonance), resistance, or other sensors know to those of skill in the art.

EXAMPLE

To test the ability of the "electronic nose" to identify molecules of interest having a particular biological activity selected from a library of molecules of interest, a quantitative structure-activity relationship (QSAR) was used to predict the inhibitory action of a series of alcohols on cytochrome P-450 aniline p-hydroxylation.

Polymer synthesis and preparation. Polymers were generally dissolved in tetrahydofuran, except for poly(4-vinylpyridine) and poly(vinylpyrrolidone), which were dissolved in ethanol, and poly(ethylene-co-vinyl acetate)(18% vinylacetate), 1,2-poly (butadiene),and poly(butadiene) (36% cis and 55% trans 1–4), which was dissolved in toluene. Each polymer (160 mg) was dissolved in its respective solvent (20 ml) either at room temperature or by heating to 35–40° C. for several hours. Carbon black (40 mg) was added and the suspension sonicated for at least 20 minutes.

Sensor Fabrication. Corning microscope slides were cut into 10 mm×25 mm pieces to provide substrate for the sensor. A 7–8 mm gap across the middle of each piece was masked while 300 nm of chromium and then 500 nm of gold was evaporated onto the ends of the slides to form the electrical contacts. Sensors were formed by spin-coating polymer/carbon black suspensions onto the prepared substrates. The resulting films were then allowed to dry overnight.

Measurements. An automated flow system consisting of LabVIEW software, a pentium computer, and electronically controlled solenoid valves and mass flow controllers were used to produce and deliver selected concentration of solvent vapors to the detectors. To obtain the desired analyte concentration, a stream of carrier gas was passed through a bubbler that had been filled with the solvent of choice. Saturation of the carrier gas with the solvent vapor was verified through measurement of the rate of mass loss of the solvent in the bubbler. The vapor-saturated carrier gas was then diluted with pure carrier gas through the use of mass flow controllers (MKS Instruments, Inc). The carrier gas for all experiments was oil-free air, obtained from the general compressed air laboratory source, containing 1.10+/−0.15 parts-per-thousand (ppth) of water vapor. The air was filtered to remove particulates but deliberately was not dehumidified or otherwise purified to reproduce a range of potential "real world" operating environments. Calibration of the flow system using a flame ionization detector (model 300 HFID, California Analytical Instruments, Inc.) Indicated that the delivered analyte concentrations were present.

Eight bubblers for generation of vapors were available, so the 22 alcohols and 2 diols were divided in 3 groups of 8 as indicated in FIG. 5. To pre-condition the sensors, prior to each of the 3 runs, the sensors were subjected to 40 exposures, 5 to each of the 8 analytes. Data collection then consisted of a set of 10 exposures to the 8 analytes, with 80 exposures performed in randomized order to eliminate systematic errors from history effects. In the third run, bubbler 2 was replaced by a pyrex tube 37 cm in length with a 1 cm inner diameter. This tube was loaded with approximately 25 cm of granular, solid neopentanol. Flow rates were calculated to give 100 ml/min of saturated vapor from the bubblers, which were of sufficient path length to provide saturated vapors. The background air flow was 1900 ml/min, so that the analyte concentration delivered to the sensors was 5% of the analyte's saturated vapor pressure at room temperature. The ability of the vapor delivery system to provide the expected analyte concentrations based on the input and control settings to the mass flow controllers as verified using a calibrated flame ionization detector that sampled several test analyte gas streams being delivered to the sensor chamber.

An exposure had 300 seconds of background air flow, followed by 300 seconds of flow of analyte at 5% of its saturated vapor pressure, followed by 300 seconds of the background air. The DC resistance of each sensor was measured at intervals of approximately 6 seconds using a multiplexing ohmmeter. The baseline resistance of a sensor was taken as an average of all measurements of the resistance of that sensor acquired over a 60 second period that started between 60 and 66 seconds prior to the start of the exposure to an analyte. The exact initiation time of this baseline resistance measurement was different for each sensor, due to small variations in the time interval required to read the set of 20 resistance values through the multiplexing ohmmeter. The resistance response for each sensor to an analyte was taken as an average of all measurements for that sensor in a 60 second period that started between 234 and 240 seconds after the beginning of the presentation of the vapor to the sensors, with the exact initiation time for each sensor channel staggered similarity to that of the baseline resistance readings. A response was taken to be the change in resistance of a sensor, $\Delta R$, divided by its baseline resistance, R. All differential resistance values ($\Delta R/R$) used in the data analysis represented, or very closely approximated, the steady-state resistance readings obtained from the sensors during exposure to the analyte of interest.

Data Analysis. Initial raw data manipulation and calculation of responses was performed using Microsoft Excel. Multiple Linear regression (MLR) was performed using either Excel or the QSAR {(Define)} module of the Cerius2 program (Molecular Simulations, Inc.) on a Silicon Graphics O2 computer. Many possible MLR models were created, compared, cross-bred, and evolved by the genetic function approximation on Cerius2.

Figure 2:
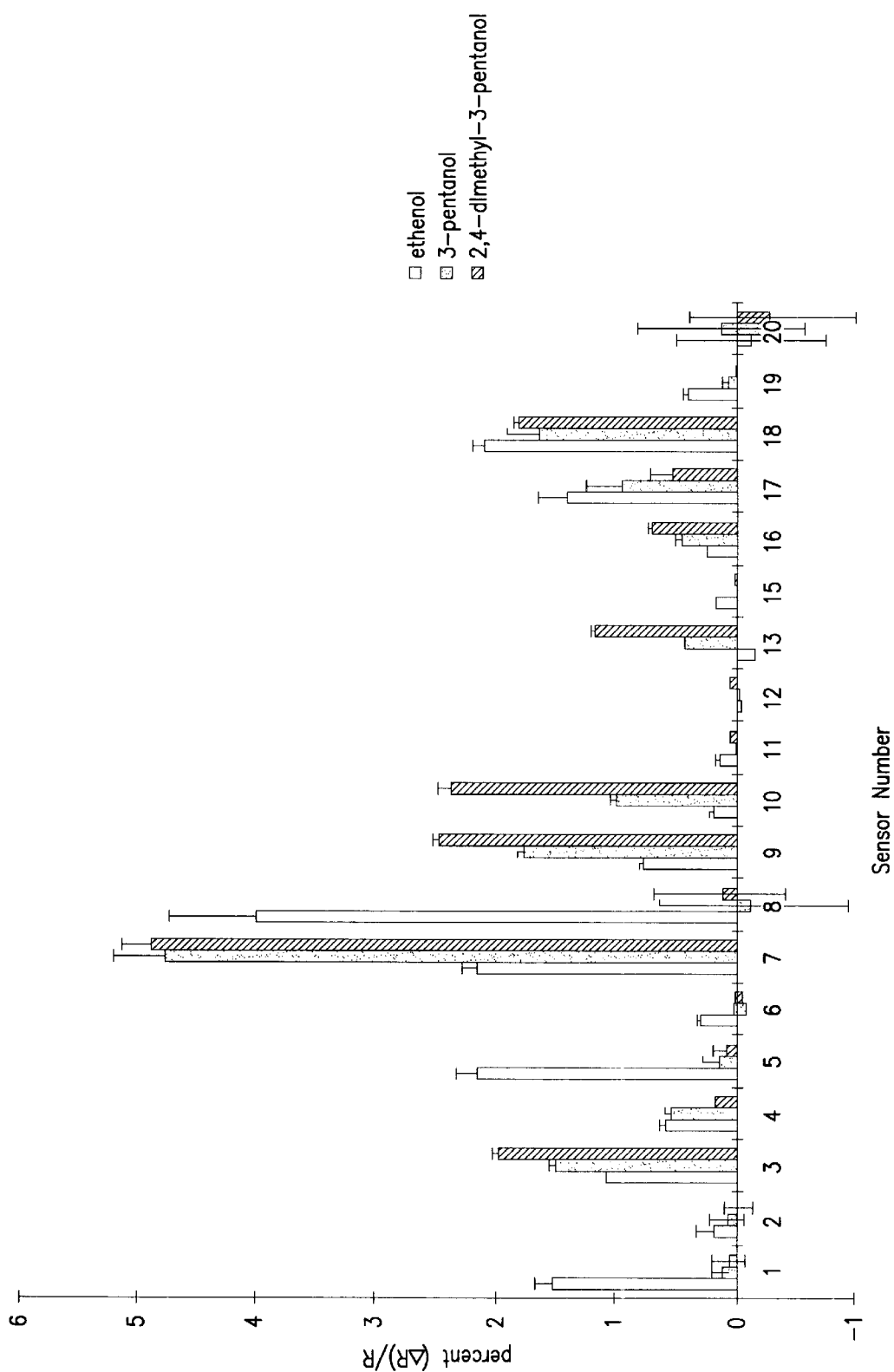
FIG. 2 presents the relative differential resistance responses for various conducting polymer composite sensors to three representative alcohols.

Results. FIG. 2 presents the relative differential resistance responses for various conducting polymer composite sensors to three representative alcohols, and FIG. 5 summarizes all of the sensor response data for the various alcohols investigated in this work. Each alcohol produced a distinct, characteristic response pattern with the array of sensors chosen for use in the work. Other sensor arrays comprising different polymer formulatives are clearly capable of providing response patterns useful in the present invention.

The responses of the 19 working sensors to 20 of the alcohols (FIG. 5) were used to build a QSAR model. Benzyl alcohol and tert-amyl alcohol were excluded from the fit because their biological activities were anomalous. The two diols were also excluded while building the model.

The inhibitory action data of Cohen and Mannering (Mol. Pharmacol. 1973, 9, 383–397) are listed in FIG. 5. The values are expressed as $pI_{50}$, where $I_{50}$ is the concentration of the alcohol (in mM) at which the activity of the enzyme is 50% inhibited, and $pI_{50}$ is the negative logarithm of $I_{50}$. More positive numbers correspond to more strongly inhibiting alcohols.

The QSAR equations consist of a linear combination of descriptors whose coefficients are obtained by a least-squares fitting of predicted to observed biological activity through multiple linear regression. Equation 1 represents a general set of QSAR equations, $$A \cdot X_{1,1} + B \cdot X_{1,2} + C \cdot X_{1,3} + \ldots + J \cdot X_{1,n} + K = Y_1 \quad (1a)$$

$$A \cdot X_{2,1} + B \cdot X_{2,2} + C \cdot X_{2,3} + \ldots + J \cdot X_{2,n} + K = Y_2 \quad (1b)$$

$$A \cdot X_{m,1} + B \cdot X_{m,2} + C \cdot X_{m,3} + \ldots + J \cdot X_{m,n} + K = Y_m \quad (1m)$$

where $Y_i$ is the biological activity of the $i^{th}$ molecule, $X_{i,j}$ is the value of the $j^{th}$ descriptor for the ith molecule, and A, B, C, ... K are constants that are obtained through the fitting of $Y_i$ (predicted) versus $Y_i$(observed). In Equation 1, the $i^{th}$ alcohol's inhibitory activity is represented by $Y_i$ and its n sensor responses are taken as its descriptors ($X_{i,1}$ to $X_{i,n}$).

The genetic function algorithm of the QSAR module of Cerius2 was used to select the best sensors for the QSAR. One hundred multiple linear regression models were generated from random combinations of 4 sensors. These models were ranked according to a lack-of-fit (LOF) parameter, as given by equation 2:

$$LOF = \frac{LSE}{(1 - ((c + dp)/m))}^2 \quad (2)$$

LSE is the least-squares error, c and p are both the number of descriptors (sets of relative differential resistance response of the sensors in the array) for a simple linear model such as the one herein, M is the number of samples (e.g., alcohols), and d is the "smoothing parameter", which is entered by the user (1.0 was used). The LOF value is therefore an inverse measure of how well the model fits the data, with a penalty for the use of a large number of descriptors relative to samples. From the set of 100 models, two "parents" are chosen, with a probability inversely proportional to their LOF, and "crossed over"—some of the descriptors from each are used to form a new model. There is then a probability for "mutation", where a new, randomly chosen, descriptor is added to the "daughter". If the daughter is not already present in the population, it replaces the model with the worst LOF from the population. After 5,000 rounds of genetic operation, convergence is generally reached, in which the optimal models have been found.

When the 19 sets of responses from the working sensors were given to the Genetic Function Algorithm (GFA), a model that incorporated 5 of the sensors was found to be optimal. The best fit is described by equation 3:

$$pI_{50}=0.51\text{-}\mathbf{3} +1.90\text{-}\mathbf{9}\text{-}3.58\text{-}\mathbf{13}\text{-}2.14\text{-}\mathbf{15}\text{-}0.90\text{-}\mathbf{18}\text{-}1.29 \quad (3)$$

n=20 R=0.995 s=0.092 F=297

Figure 3:
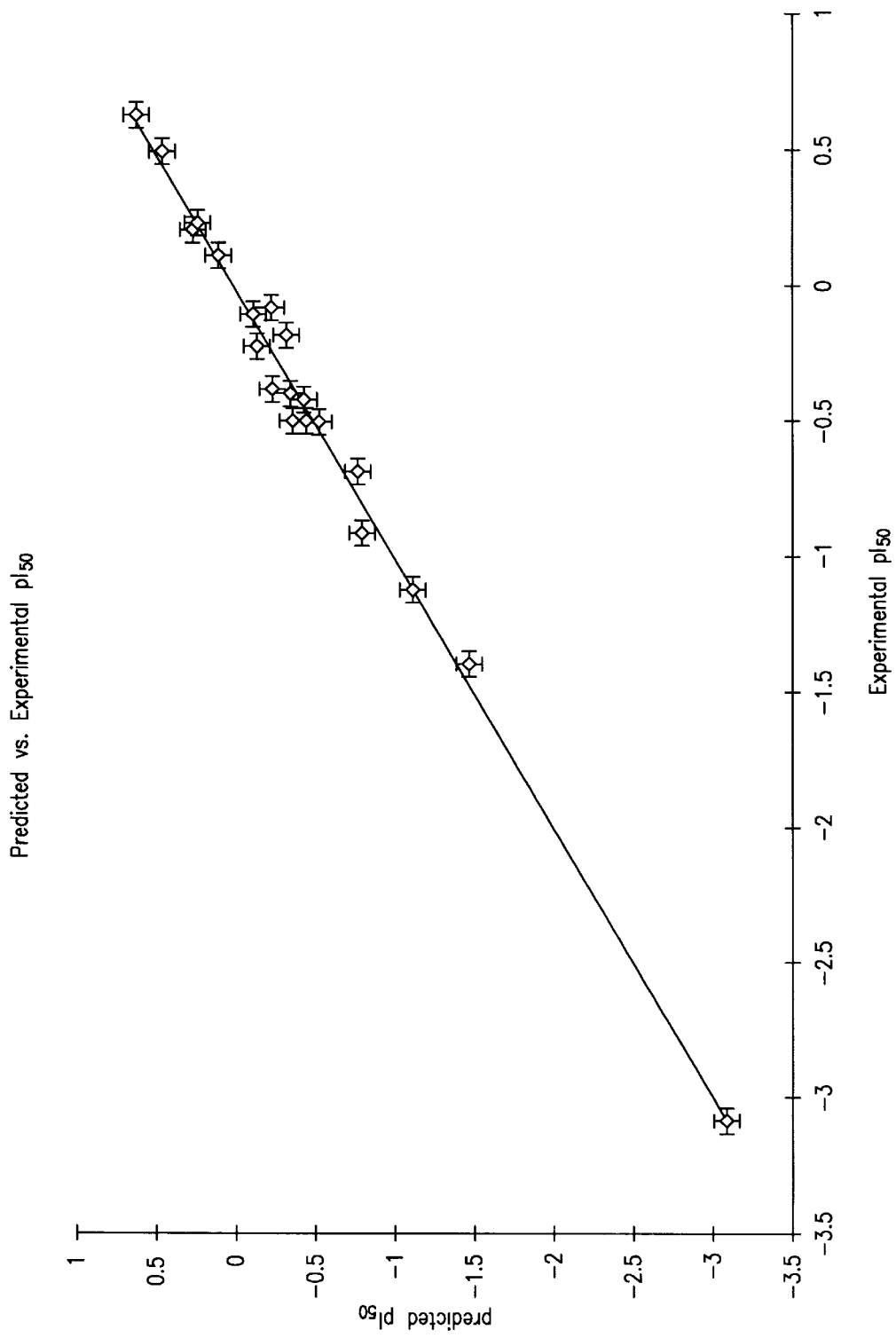
FIG. 3 shows a plot of $pI_{50}$ predicted by equation 3 versus the actual experimental value. Horizontal error bars represents an average experimental error and vertical error bars correspond to the standard error of equation 3. The line represents perfect agreement between experiment and prediction.
Figure 4:
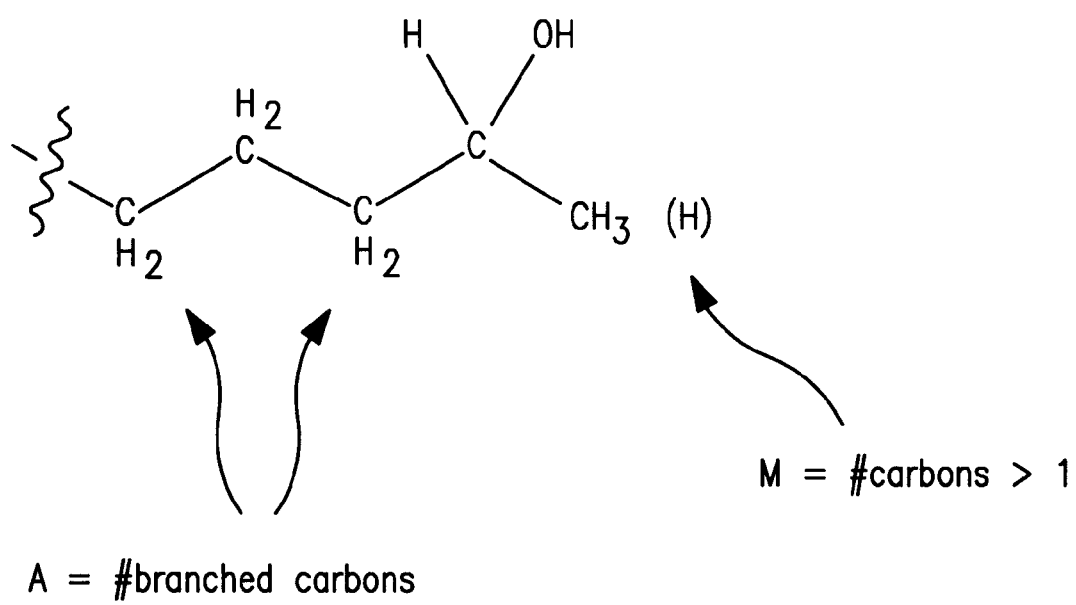
FIG. 4 shows a diagram illustrating the M and A steric parameters.

The numbers in bold refer to sets of responses from the sensors with those numbers, n is the number of samples, R is the correlation coefficient, and s is the standard error. The correlation coefficient of 0.995 indicates that the fit was quite good. The F statistic of 297 indicates that the overall significance of the fit is very high, in fact is at a level of $1-10^{-13}$. Coefficients for all sensors are significant far beyond the 99.9% level, as attested to by their t statistics (see table 3). Predicted versus experimental $pI_{50}$ values are plotted in FIG. 3.

TABLE 3

Regression Statistics For the Coefficients of Equation 3

|  | Coefficient | Standard Error | t Stat | P-value |
| --- | --- | --- | --- | --- |
| Intercept | -1.29 | 0.27 | -4.71 | 3.32E-04 |
| 3 | 0.51 | 0.07 | 6.93 | 6.98E-06 |
| 9 | 1.90 | 0.19 | 9.92 | 1.03E-07 |
| 13 | -3.58 | 0.21 | -17.13 | 8.70E-11 |
| 15 | -2.14 | 0.27 | -7.91 | 1.56E-06 |
| 18 | -0.90 | 0.08 | -11.34 | 1.94E-08 |

The t statistic is equal to the value of the coefficient divided by its standard error; it is used to derive the P value, which indicates the significance of the coefficient.

Methanol has an inhibition activity distinctly different from that of the other alcohols, and this can lead to a misleadingly good fit through a "point and cluster" effect. A second least-squares fitting of equation 3 was performed with the exclusion of methanol. The coefficient of 15 changed from -2.14 to -2.20, while those of the other sensors remained nearly the same. The overall quality of the fit declined; F decreased from 297 to 109, corresponding to a decrease in the significance of the fit from the level of $1-(1\times10^{-13})$ to $1-(4\times10^{-10})$. The decrease quality of the fit occurs because methanol is modeled well by the equation, but when methanol is excluded there is much less variation in the data to be fit.

Electronic Nose-Based QSAR. The selection of which molecules to include in a QSAR is crucial. In the sense, that it is desirable to use the broadest set of molecules available to build a QSAR, while not including only one or two molecules from a distinctly different class of compounds. For example, benzyl alcohol, the only aromatic alcohol in the data set, has a higher activity than is predicted by both our QSAR and another QSAR on the cytochrome P-450 system. The anomalous activity of benzyl alcohol could be accounted for with an additional descriptor unique to benzyl alcohol, but the choice of such a parameter is rather arbitrary, so benzyl alcohol was excluded during the building of our QSAR. Tert-amyl alcohol was also excluded because there is evidence that tertiary alcohols function through a stimulatory mechanism in addition to the usual inhibitory mechanism. As would be expected in tert-amyl alcohol were also acting through this stimulatory mechanism, its inhibitory activity is anomalously low. The two diols were also excluded while building the model. Because of these limitations, the QSAR is expected to be most successful at predicting the activity of aliphatic mono-alcohols having no other functionalities.

The sensors chosen for the model by the GFA are among those whose responses are most reproducible. Reproducibility was measured by examining the set of 10 response of a given sensor to a given analyte. The value $S_{i,j}$ is defined as the standard deviation among the 10 responses of the $j^{th}$ sensor to the $i^{th}$ alcohol divided by the average of those responses. Each sensor has a set of 20 S values, one for each alcohol. A sensor's reproducibility can be gauged by the median of its set of S values. Four of the five sensors used in the model displayed median S values less than 0.063, raking them among the best seven sensors. The only sensor outside this group, 15, responded only to very polar analytes. Since its response to the majority of the analytes was quite small, its S value for those analytes is very large. However, for the analytes to which it did respond, for example methanol and ethanol, its S values are small, 0.040 and 0.041, respectively. The inclusion of 15 might be questioned if it were necessary only to model the activity of one analyte, namely the outlier methanol. To test the validity of including 15 in the QSAR, equation 3 was refit with the same set of sensors and all of the previously used alcohols, excluding methanol. In the new QSAR, the significance of 15 remains significant. If the set of five sensor responses to methanol are substituted into the second QSAR equation, which was formed with no information about methanol, the predicted $pI_{50}$ of methanol is −3.12 very close to its experimental value of −3.09. It appears that whatever molecular characteristics are probed by 15 are successfully extrapolated from the more moderately polar analytes to methanol. In other words, 15 is not just an indicator variable for methanol that is fit with an arbitrary coefficient.

A quantitative measure of the predictive power of the QSAR can be obtained by building a model using the biological and sensor response data from all the molecules except one, and then predicting the activity of the excluded molecule with that model. The procedure is repeated for each molecule in the data set, and the predictive sum of squares (PRESS) is defined as the sum, over all analytes, of the squared differences between the predicted and actual biological activity. Using equation 3, the PRESS for the set of 20 alcohols is 0.221. This value can be compared to the residual sum of squares, RSS, in which one QSAR equation (fit to all samples) is used to calculate the predicted activity. As would be expected, the RSS of 0.117 is lower than the PRESS. More significantly, a large difference between the PRESS and RSS would imply that the model had used too many parameters and overfit the data, and this appears not to be the case.

An optimum fit (as judged by the LOF parameter) was found to require five descriptors; no equation with a different number of descriptors formed as significant a model. The best 4 sensors QSAR, consisting of sensors 1, 13, 16 and 17, has an R=0.984, s=0.163, and F=114, indicating an overall significance at the level of $1-(5\times10^{-11})$. On the other hand, addition of further sensors adds parameters and enables a better fit to the data set. However, if 4 is added to equation 3 to form the best 6-sensor equation, certain key statistics point to a diminished model. As would be expected with an additional parameter, R increases, from 0.995 to 0.996. Additionally, the standard error decreases from 0.0916 to 0.0834, the RSS decreases from 0.117 to 0.090, and the F statistic increases from 297 to 300. However, the significance of the fit, represented by the F statistic, decreases from $1-(1.08\times10^{-13})$ to $1-(3.66\times10^{-13})$. The PRESS increases from 0.221 to 0.253. Thus, although the 6-sensor model fits the set of 20 alcohols better than the 5-sensor model, the 6-sensor model is worse at predicting the activity of an alcohol that was not included in the fit, indicating that the 6-sensor model has overfit the data.

As described above, the cytochrome P-450 p-hydroxylation inhibition activities of all the aliphatic mono-alcohols investigated in this work could be quite accurately predicted from a model that was constructed without the use of any information about the molecular structure of the alcohols for which the prediction are made. This indicates that the resistance data output of the electronic nose contains implicit information on most of the chemical factors that control the interactions of the enzyme with the alcohols. These resistance data reflect the binding interactions between the alcohols and a collection of polymers having a diverse collection of chemical attributes. It is not necessary that an individual polymer probe specifically and exclusively one such descriptor of the analyte-substrate interaction, because the desired information can be obtained through analysis of the collective response of the sensor array to an analyte.

Comparison with Other QSARS. Cohen and Mannering fit the activity of 11 of the unbranched 1–and 2-alcohols (excluding methanol) to a one parameter equation using log P (J. Mol. Pharmaco. 1973, 9, 383–397). A modified version, using updated log P values and fit to only 10 alcohols (excluding methanol and ethanol), was given later by Shusterman (equation 4) (Chem.-Biol. Interactions 1990, 74, 63–77).

$$pI_{50}=0.43\log P-0.53 \qquad (4)$$

N=10 R=0.954 s=0.128

However, Shusterman also showed that for a larger set of alcohols, a simple fit to log P was inadequate to describe most of their activity; a fit of 19 alcohols yielded equation 5, which has rather poor regression statistics.

$$pI_{50}=0.35\log P-0.71 \qquad (5)$$

n=19 R=0.505 s=0.468

In a second equation using two descriptors, log P and (log p)2, Cohen and Mannering fit 17 of the alcohols with an R of 0.98 (equation 6).

$$pI_{50}=1.50 \log p -0.36(\log p)^2+1.75 \qquad (6)$$

n=17 R=0.98 s=0.44

Although this was a better fit, it used more descriptors. Additionally, it is evident from inspection of the data that there are factors besides hydrophobicity that determine an alcohol's activity. Four subsequent QSARs have therefore been used to model; the data set more fully and some aspects of these models are discussed below.

A more complex, three parameter, QSAR was based upon logP, a calculated electronic parameter ($\epsilon_{HOMO}$), and a steric parameter ($BULK_{lat}$) (equation 7).

$$pI_{50}=16.2\log P-16.0\log(\beta P+1)-1.35 BULK_{lat}+0.381\epsilon_{HOMO}+22.5 \quad (7)$$

n=21 R=0.982 s=0.170 log$\beta$=1.05

Shusterman and Johnson, however, pointed out that the use of $\epsilon_{HOMO}$ as a parameter was unjustified since it was necessary only to fit benzyl alcohol, and becomes an insignificant parameter (as indicated by its t value) when benzyl alcohol is excluded from the data set. Similarly, the bilinear dependence of $pI_{50}$ upon log P of equation 7 was necessary only to fit a single data point, methanol.

Another QSAR, based on a choice of molecular connectivity indices, has also been used to model the activity of 20 alcohols (benzyl alcohol and tert-amyl alcohol were excluded (equation 8).

$$pI50 = -6.88(1/{}^0\chi^v) - 1.14{}^4\chi_{PC} + 1.85 \quad (8)$$

n=20 R=0.983 s=0.156

The parameter ${}^0\chi^v$, the zero-order valence molecular connectivity index, basically corresponds to molecular size, and therefore hydrophobicity, for this set of molecules. Hence, the inverse of the index has a negative coefficient in equation 8. The parameter ${}^4\chi_{pc}$, the fourth-order path/cluster molecular connectivity index, correlates with the degree of branching in the molecule, and therefore also has a negative coefficient in equation 8.

A third QSAR, which relies entirely upon calculated electronic parameters as descriptors, has been constructed and used to fit all 22 alcohols. Shusterman noted problems with the QSAR. For example, it was asserted that the a-carbon of the alcohols was acting as an electron acceptor from the enzyme, because a correlation between activity and QCL, the electron density on the α-carbon in the LUMO, was found. QCL is correlated with log P(R=0.747), to some extent explaining the fit. Two alcohols, 3- methylbutanol and 2,4-dimethyl-3-pentanol, were poorly fit, and no rationalization was presented for why the correlation with QCL would not apply to these two substrates as well.

Finally, Shusterman created a QSAR based on log P and two steric parameters, M and A, which were used to describe the branching of the alcohols. M is the number of carbons beyond the methyl substituent in FIG. 3, thus, 1- and 2-alcohols have an M=0, while M for 3-pentanol would be one, and for 2,4-dimethyl-3-pentanol is 2. The second parameter, A, refers to the number of branched carbons in the main chain, A=1 for 2-methyl-1-butanol and 2 for neopenyl alcohol. A fit of 19 of the alcohols (benzyl alcohol, tert-amyl alcohol, and methanol were excluded) yielded equation 9. The negative coefficient for M and A indicate the loss of activity with branching.

$$pI50 = 0.48 \log P - 0.65 \cdot M - 0.31 \cdot A - 0.60 \quad (9)$$

n=19 R=0.955 s=0.171

To compare the electronic nose QSAR to those of Sabljic and Shusterman, one must use statistics that take into account the number of descriptors used. Table 4 lists the comparison of selected regression statistics from the QSAR of Sabljic, Shusterman, equation 3, and the QSAR created when the coefficients of equation 3 were fit to the 19 alcohols besides methanol (R is the correlation coefficient, s is the standard error, and the final column is the overall significance of the regression equation). Because the electronic nose QSAR model uses more parameters, it is inappropriate to compare just either the correlation coefficients, standard error, or residual sum of squares of the models. To some extent, the PRESS should be independent of the number of parameters in a model, since the model is tested upon molecules about which it has no information. The PRESS of the electronic nose QSAR model is significantly lower than the other two models of interest. Finally, the F steatitic gauges the overall significance of the fit while accounting for the number of parameters used. By this measure, the electronic nose QSAR is approximately as significant as Sabljic's and more significant than Shusterman's.

TABLE 4

|  | Data pts fit | descriptors used | R | s | RSS | PRESS | F | Significance F |
|---|---|---|---|---|---|---|---|---|
| Sabljic | 20 | 2 | 0.983 | 0.156 | 0.414 | 0.872 | 250 | 2.51E − 13 |
| Shusterman | 19 | 3 | 0.956 | 0.17 | 0.436 | 0.786 | 53 | 3.34E − 08 |
| Present Disclosure | 20 | 5 | 0.995 | 0.092 | 0.117 | 0.221 | 297 | 1.08E − 13 |
| Present Disclosure (no methanol) | 19 | 5 | 0.988 | 0.095 | 0.117 | 0.243 | 109 | 3.89E − 10 |

It appears that the important chemical interaction involved in the partitioning of the aliphatic alcohols into the enzyme binding site are probed by the array responses. The construction of our QSAR did not require making assumption regarding which steric or electronic factors are important or what parameters to use to capture such effects. Obtaining chemical insight into the nature of the dominant binding forces involved in the reaction being modeled would require a complete understanding of the chemical factors that determine the analyte partitioning into each polymer in the electronic nose. In principle it is possible to extract such information for certain descriptors of interest, but it is not necessary to have such information in order to use the readily-obtained electronic nose data to predict successfully the activity of various alcohols in inhibiting cytochrome P-450 activity.

Although only a few embodiments have been described in detail above, those having ordinary skill in the art will certainly understand that many modifications are possible in the preferred embodiment without departing from the teachings thereof.

All such modifications are intended to be encompassed within the following claims.

What is claimed is:

1. A method for screening analytes for a specific activity, chemical or physical property, or function, comprising the steps of:
   a) contacting an array comprising a plurality of different differentially responsive sensors with an analyte of interest comprising an activity, property, or function, wherein each of the plurality of sensors in the array are responsive to a plurality of analytes having differing properties;
   b) measuring a signal output from each sensor of the plurality of different differentially responsive sensors;

c) using the results of said measuring to obtain a signal profile related to a change in the signal output from each sensor; and d) comparing the signal profile to at least one previously-obtained signal profile obtained from a standard sample not including the analyte of interest and which has a known specific activity, chemical or physical property, or function, wherein such comparison is used to indicate a specific activity, function, or chemical or physical property of the analyte of interest.

2. The method of claim 1, wherein the analyte of interest is a chemical.

3. The method of claim 2, wherein the chemical is a biochemical.

4. The method of claim 3, wherein the biochemical is selected from the group consisting of a lipid, hormone, fatty acids, nucleic acid, polypeptide, and carbohydrate.

5. The method of claim 4, wherein the polypeptide is selected from the group consisting of an antibody, enzyme, and protein.

6. The method of claim 5, wherein the antibody is a monoclonal antibody, polyclonal antibody, humanized antibody, or fragments thereof.

7. The method of claim 5, wherein the enzyme is selected from the group consisting of lipases, esterases, proteases, glycosidases, glycosyl transferases, phosphatases, kinases, mono- and dioxygenases, haloperoxidases, lignin peroxidases, diarylpropane peroxidases, eposide hydrolases, nitrile hydrotases, nitrilases, transaminases, amidases, and acylases.

8. The method of claim 2, wherein the chemical is an organic selected from the group consisting of alkanes, alkenes, alkynes, dienes, alicyclic hydrocarbons, arenes, alcohols, ethers, ketones, aldehydes, carbonyls, carbanions, polynuclear aromatics and derivatives thereof.

9. The method of claim 1, wherein the specific activity is selected from the group consisting of enzymatic activity, binding activity, inhibitory activity, and modulating activity.

10. The method of claim 1, wherein the different differentially responsive sensors change optically, electrically, magnetically, mechanically, physically, or combinations thereof.

11. The method of claim 1, wherein the different differentially responsive sensor is selected form the group consisting of crystalline colloidal array (CCA) containing sensors, metal oxide sensors, dye-impregnated polymers coated onto beads or optical fibers, bulk conducting organic polymers, capacitance sensors, chemically-sensitive resistor sensors, and combinations thereof.

12. The method of claim 1, wherein the chemical or physical property is selected from the group consisting of side groups, charge, hydrophobicity, polarity, molecular size or shape, and chirality.

13. The method of claim 1, wherein the different differentially responsive sensors are chemically sensitive resistors.

14. A method of screening an analyte for a specific activity, chemical or physical property, or function comprising the steps of:

a) measuring outputs from an array comprising a plurality of chemically-sensitive resistors, each resistor comprising a conductive material and a non-conductive material, wherein the plurality of chemically sensitive resistor in the array are responsive to a plurality of analytes;

b) using results of said measuring to obtain a signal profile, related to a change in resistance in the plurality of resistors; and c) comparing the signal profile to at least one previously-obtained signal profile obtained from a standard sample not including the analyte of interest and which has a known specific activity, chemical or physical property, or function, wherein such comparison is used to indicate a specific activity, function, or chemical or physical property of the analyte of interest.

15. The method of claim 14, wherein the analyte is a chemical.

16. The method of claim 15, wherein the chemical is a biochemical.

17. The method of claim 16, wherein the biochemical is selected from the group consisting of a lipid, hormone, fatty acids, nucleic acid, polypeptide, and carbohydrate.

18. The method of claim 17, wherein the polypeptide is selected from the group consisting of an antibody, enzyme, and protein.

19. The method of claim 18, wherein the antibody is a monoclonal antibody, polyclonal antibody, humanized antibody, or fragments thereof.

20. The method of claim 18, wherein the enzyme is selected from the group consisting of lipases, esterases, proteases, glycosidases, glycosyl transferases, phosphatases, kinases, mono- and dioxygenases, haloperoxidases, lignin peroxidases, diarylpropane peroxidases, eposide hydrolases, nitrile hydrotases, nitrilases, transaminases, amidases, and acylases.

21. The method of claim 15, wherein the chemical is an organic selected from the group consisting of alkanes, alkenes, alkynes, dienes, alicyclic hydrocarbons, arenes, alcohols, ethers, ketones, aldehydes, carbonyls, carbanions, polynucliear aromatics and derivatives thereof.

22. The method of claim 14, wherein the specific activity is selected from the group consisting of enzymatic activity, binding activity, inhibitory activity, and modulating activity.

23. The method of claim 14, wherein the resistor comprised of regions of a non-conductive material and regions of a conductive material compositionally different than the non-conductive material, each resistor providing an electrical path through the regions of conductive and non-conductive material, wherein interaction of the sample with the resistor provides a change in resistance in the material.

24. The method of claim 14, wherein the signal profile of the standard sample is derived from a library.

25. The method of claim 24, wherein the library is generated by a neural network.

26. The method of claim 14, wherein the chemical or physical property is selected from the group consisting of side groups, charge, hydrophobicity, polarity, molecular size or shape, and chirality.

* * * * *